United States Patent
Kalloo et al.

(10) Patent No.: US 8,233,996 B2
(45) Date of Patent: Jul. 31, 2012

(54) DEVICES AND METHODS FOR TREATMENT OF GASTROINTESTINAL DISORDERS

(75) Inventors: Anthony Nicholas Kalloo, Bowie, MD (US); Sergey Veniaminovich Kantsevoy, Owings Mills, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 12/962,911

(22) Filed: Dec. 8, 2010

(65) Prior Publication Data

US 2011/0077662 A1   Mar. 31, 2011

Related U.S. Application Data

(63) Continuation of application No. 11/885,938, filed on Feb. 27, 2009, which is a continuation of application No. PCT/US2006/009138, filed on Mar. 13, 2006.

(60) Provisional application No. 60/660,680, filed on Mar. 11, 2005.

(51) Int. Cl.
*A61N 1/00* (2006.01)

(52) U.S. Cl. .................................................. 607/133

(58) Field of Classification Search .............. 607/113, 607/2, 40, 62; 600/115; 604/67
See application file for complete search history.

(56) References Cited

U.S. PATENT DOCUMENTS

| | | | |
|---|---|---|---|
| 6,895,279 B2 * | 5/2005 | Loeb et al. | 607/40 |
| 7,606,623 B2 * | 10/2009 | Ludlow et al. | 607/62 |
| 2002/0123774 A1 * | 9/2002 | Loeb et al. | 607/40 |
| 2002/0165589 A1 | 11/2002 | Imran et al. | |
| 2005/0020970 A1 * | 1/2005 | Gerber | 604/67 |
| 2005/0245788 A1 * | 11/2005 | Gerber | 600/115 |
| 2006/0015125 A1 * | 1/2006 | Swain | 606/151 |
| 2006/0036293 A1 * | 2/2006 | Whitehurst et al. | 607/40 |
| 2006/0095079 A1 * | 5/2006 | Gerber | 607/2 |
| 2011/0034968 A1 * | 2/2011 | Knudson et al. | 607/40 |

* cited by examiner

*Primary Examiner* — George Manuel
*Assistant Examiner* — Robert Wieland
(74) *Attorney, Agent, or Firm* — Edwards Wildman Palmer LLP; Peter F. Corless; Lisa Swiszcz

(57) ABSTRACT

An implantation device for releasably holding implantable microstimulators can be used to guide one or more microstimulators to any site within the gastrointestinal tract for implantation. The device can further releasably hold one or more ligation clips for securing the one or more microstimulators in place within the implantation site(s) and/or for closing an incision in which a microstimulator is implanted. The device can be employed using open, laparoscopic, and endoscopic techniques.

25 Claims, 17 Drawing Sheets

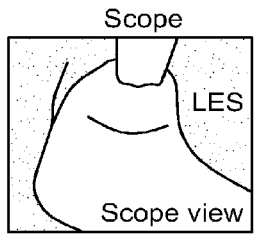
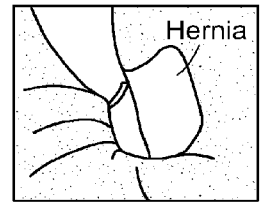
FIG. 6A'
FIG. 6B'
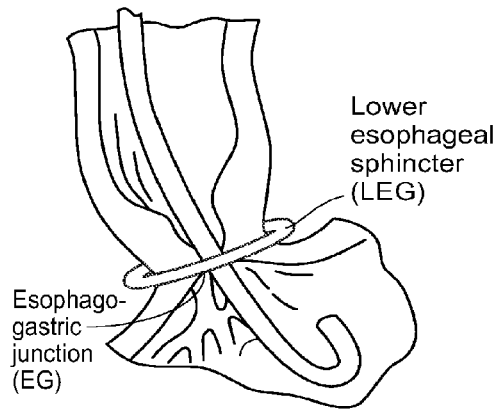
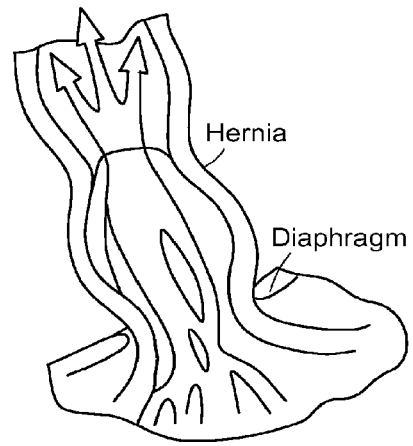
FIG. 6A
FIG. 6B
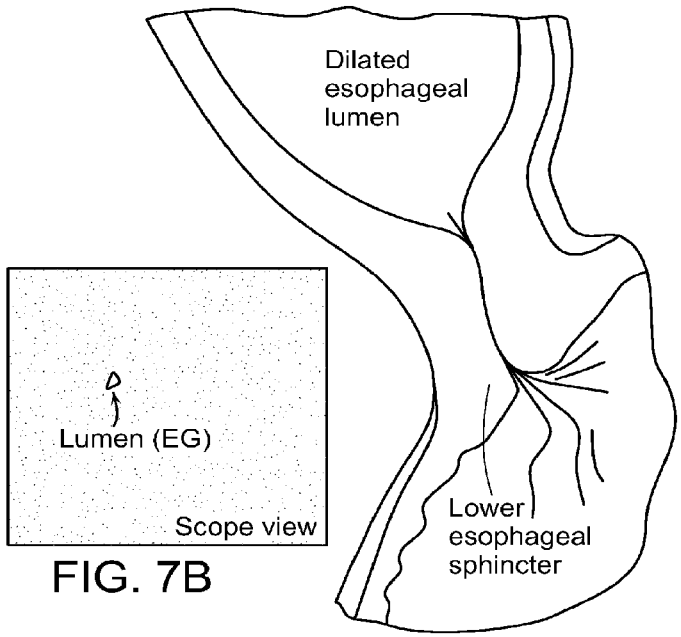
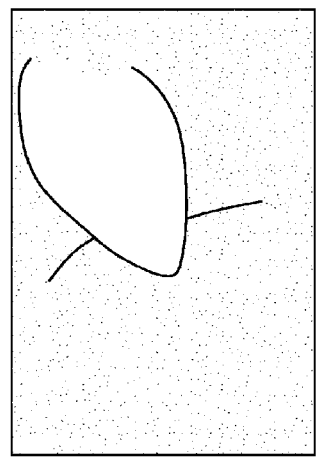
FIG. 7B
FIG. 7A
FIG. 7C

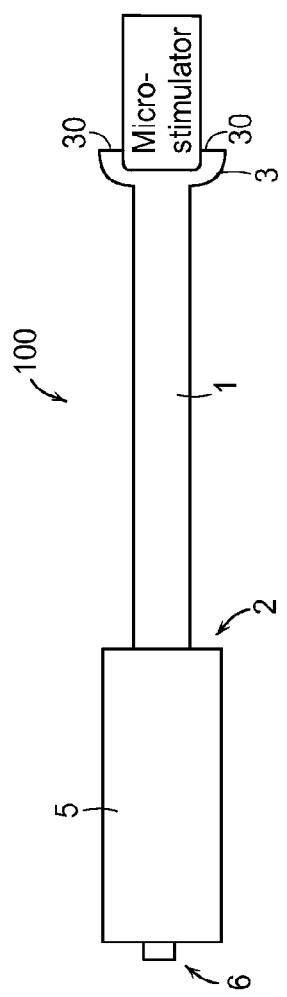
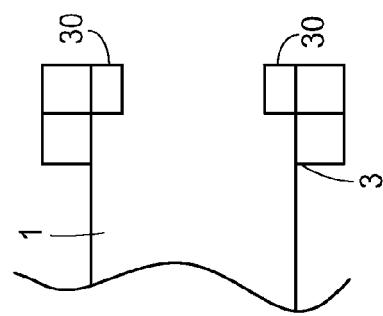
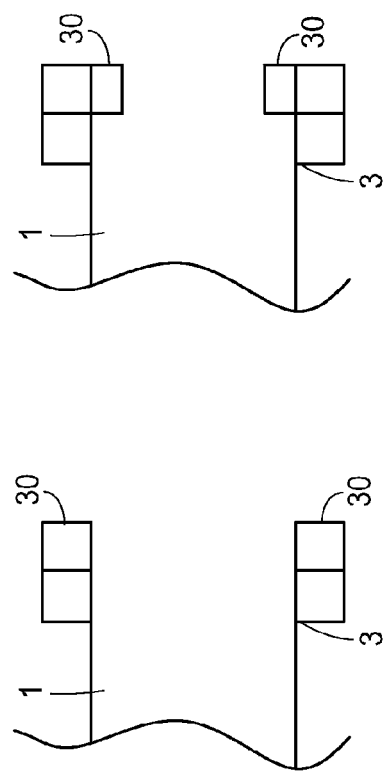

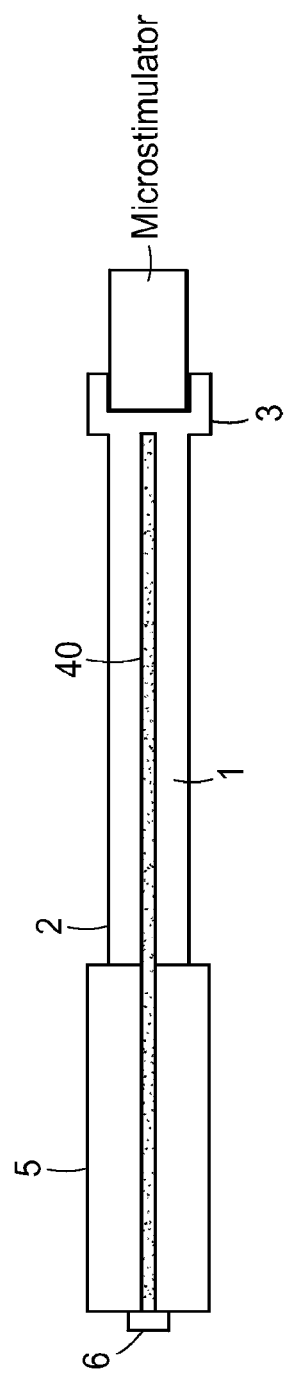
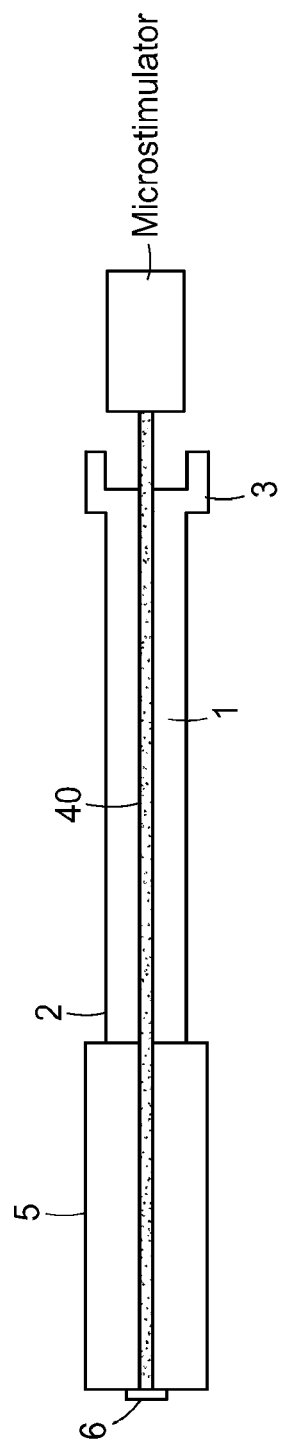

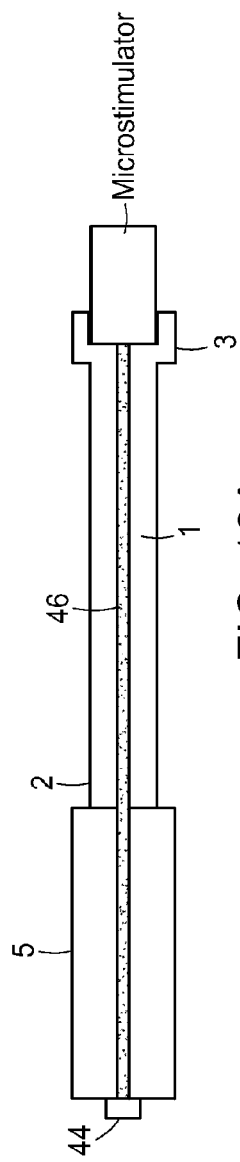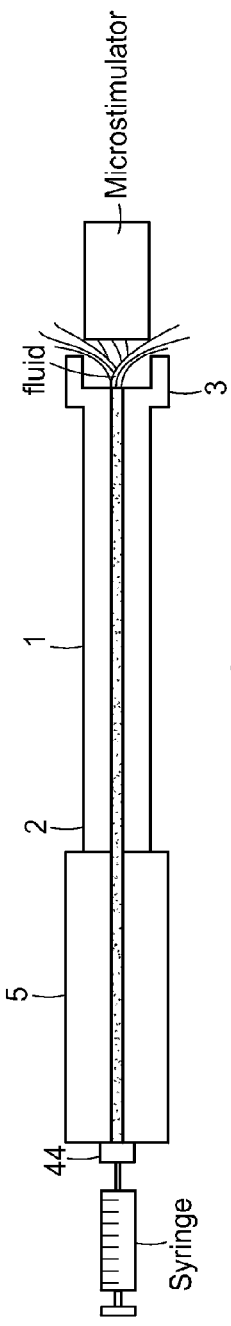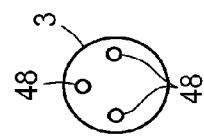

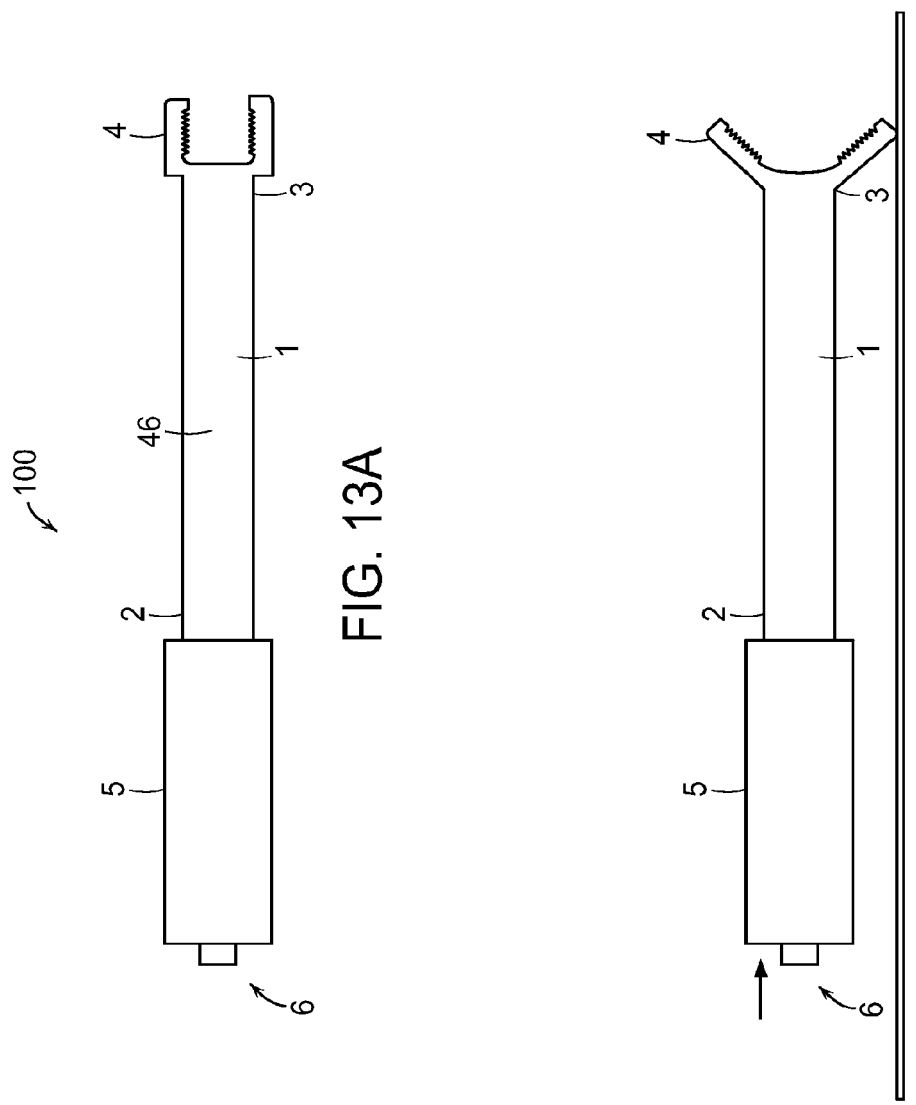

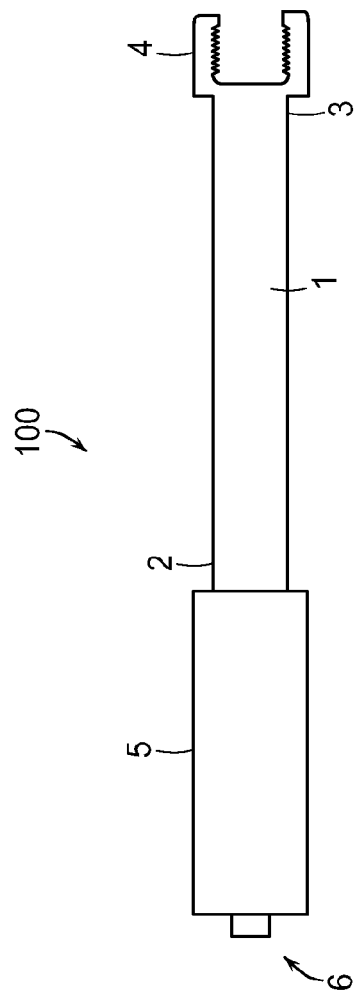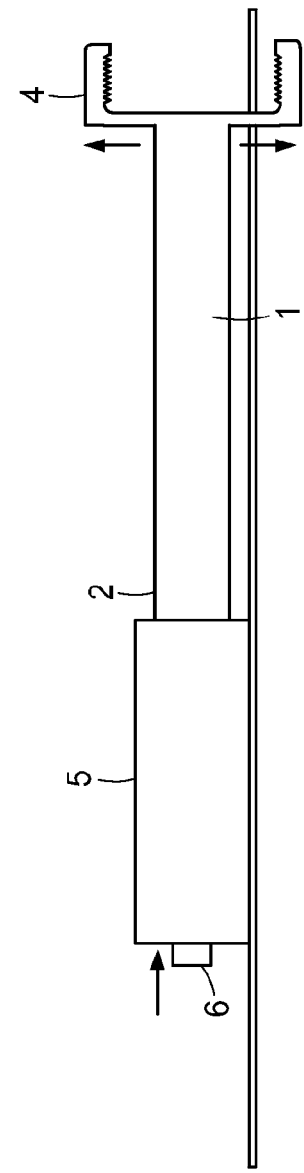

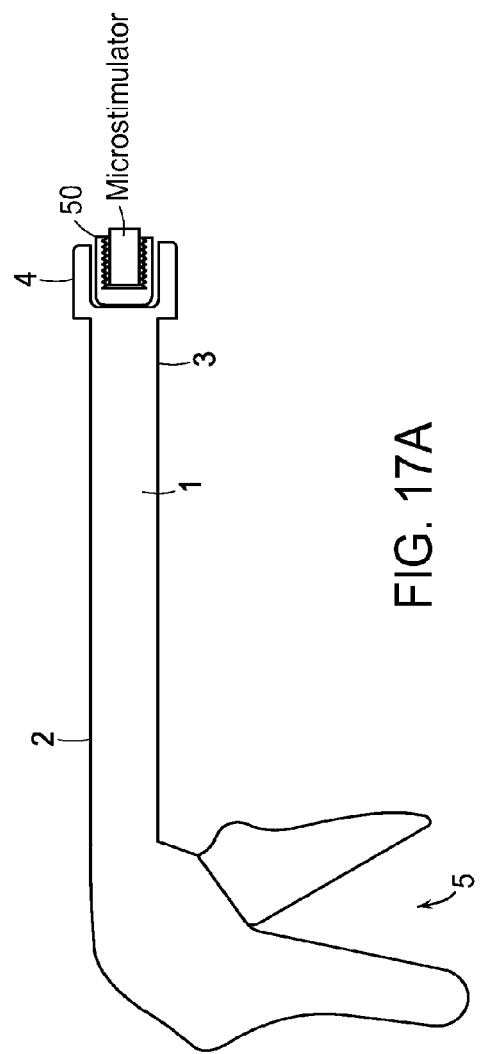
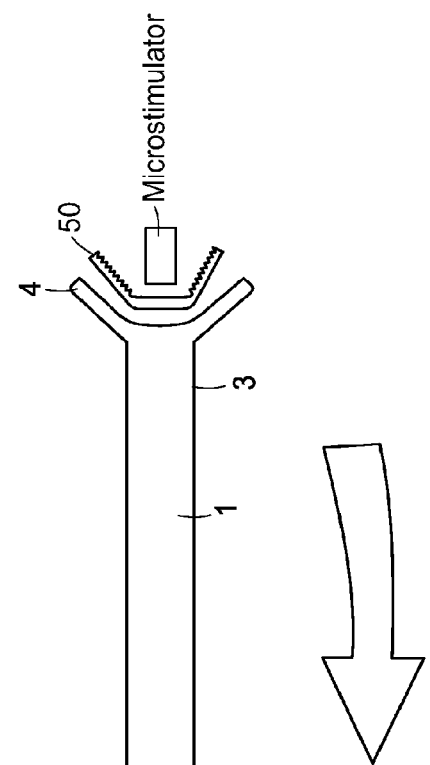
FIG. 17A
FIG. 17B

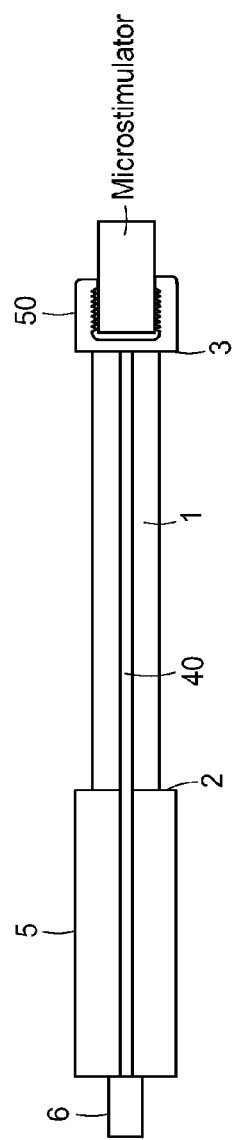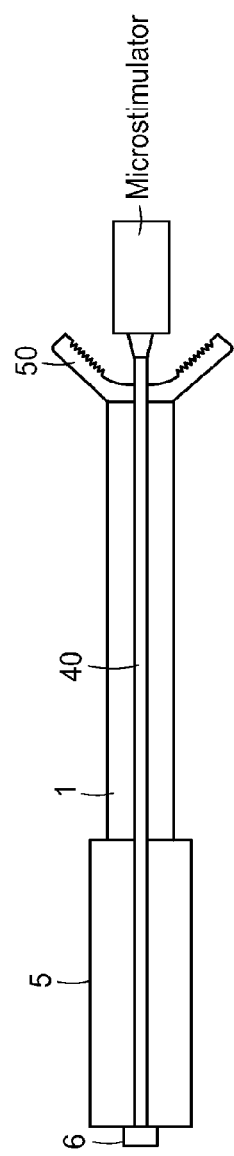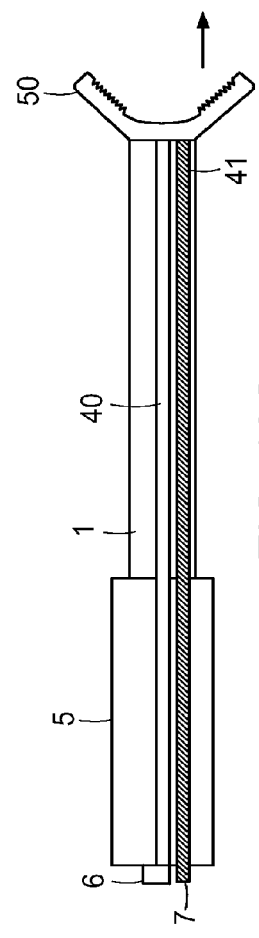

DEVICES AND METHODS FOR TREATMENT OF GASTROINTESTINAL DISORDERS

CROSS-REFERENCE TO RELATED APPLICATIONS

This application is a continuation of U.S. application Ser. No.: 11/885,938 filed Feb. 27, 2009, which is a national phase application pursuant to 35 U.S.C. § 371 of PCT/US2006/009138 filed Mar. 13, 2006, which claims priority to U.S. Provisional Patent Application Ser. No. 60/660,680 filed Mar. 11, 2005, the entire disclosures of which are incorporated herein by reference in their entireties.

TECHNICAL FIELD

The present invention generally relates to methods and devices for treating gastrointestinal (GI) disorders by implantation of microstimulators into the gastrointestinal (GI) tract.

BACKGROUND INFORMATION

In a normal human adult male, the gastrointestinal (GI) tract is approximately 7.5 meters long (25 feet) and it extends from the mouth to the anus. It consists of the upper GI tract and the lower GI tract. The upper GI tract includes the mouth (oral cavity, which includes the salivary glands, mucosa, teeth, and tongue), the pharynx, the esophagus and cardia, and the stomach (antrum and pylorus and pyloric sphincter). The lower GI tract includes the intestine and anus. The intestine is broken down into the small intestine and the large intestine. The small intestine has three parts: the duodenum, the jejunum, and the ileum. The large intestine has three parts: the cecum, the colon (ascending colon, transverse colon, descending colon, and sigmoid flexure), and the rectum. The function of the GI tract is to transfer nutrients and water from the external environment to the body.

Each part of the gastrointestinal (GI) tract performs a specialized function in the digestion of food. Digestion is regulated both hormonally and by the autonomic nervous system. The major hormones that regulate the digestive system (e.g. secretin, gastrin and cholecystokinin) are produced and released by cells in the mucosa of the stomach and small intestine. Both arms of the autonomic nervous system, the parasympathetic nerves and the sympathetic nerves, influence the digestive process. The parasympathetic nerves stimulate secretions and peristalsis, while the sympathetic influence is more inhibitory.

Digestion begins in the mouth with chewing. As the teeth break down the food, saliva moistens it to facilitate swallowing. Saliva also contains a digestive enzyme called amylase, which starts to break down some of the carbohydrates (starches and sugars) in the food. After the food is swallowed, it moves into the pharynx and then travels down the esophagus.

The esophagus is a muscular tube that extends from the pharynx through the diaphragm to connect with the stomach in the abdominal cavity. The body of the esophagus is approximately 18-25 cm long extending from the upper esophageal sphincter to the lower esophageal sphincter. The esophagus is divided into four regions: the cervical esophagus, the upper thoracic esophagus, the mid-thoracic esophagus, and the distal thoracic esophagus (FIG. 3). The upper third of the esophagus consists of striated muscle, and the lower two-thirds consists of smooth muscle. A network of intrinsic neurons, found in the muscle layers lining the lumen of the esophagus, communicates to the central nervous system via the vagus nerve, the adrenergic ganglia, and the celiac ganglia. (FIG. 3). Vagal activity increases esophageal activity. Swallowing is triggered by a signal transmitted by the vagus nerve, and the timing of the swallowing sequence (primary peristalsis) is dependent on nerves intrinsic to the esophagus. Sympathetic innervation is sensory in nature.

Before passing into the stomach, food must pass through the lower esophageal sphincter (LES), a ring of increased thickness in the smooth-muscle layer of the esophagus. The LES relaxes before the esophagus contracts, and allows food to pass through to the stomach. After food passes into the stomach, the LES constricts to prevent the contents from reentering the esophagus from the stomach. Relaxation of the LES is maintained by both muscular and nerve mechanisms. The release of acetylcholine by nerves maintains or increases LES tone. Reflex mechanisms, physiologic alterations, and ingested substances can also affect LES tone. The release of nitric oxide by nerves relaxes the LES in response to swallowing, although transient LES relaxations may also occur independent of swallowing. This relaxation is often associated with transient gastroesophageal reflux in otherwise normal people.

Once food reaches the stomach, the stomach muscles churn and mix it with acids and enzymes, breaking it into smaller pieces. Some substances, such as water, salt, sugars, and alcohol can be absorbed directly through the stomach wall, while most other substances need further digestion and must travel into the intestine before being absorbed. Parietal cells within gastric glands secrete hydrochloric acid (HCl), which makes gastric juice acidic, with a pH less than 2. During a meal, the rate of HCl production increases. Seeing, smelling, tasting, and chewing food sends information through the vagus nerves to the parietal cells, causing them to increase acid production. Stomach distention, hydrogen ion concentration, and peptides send messages through long and short neural reflexes to increase gastrin release, which increases HCl production. Before the food leaves the stomach, it is in the form of a thick liquid called chyme.

The chyme passes from the stomach into the duodenum, the first 20 to 30 cm of the small intestine, and through the small intestine for further digestion and absorption. The inner wall of the small intestine is covered with millions of microscopic, finger-like projections called villi, which are the vehicles through which nutrients can be absorbed into the body. Distention of the intestine sends both hormonal and neural reflex messages to decrease gastrin release, which decreases HCl production in the stomach.

From the small intestine, food that has not been digested and some water travels to the large intestine. By the time food reaches the large intestine, nutrient absorption is nearly finished. The large intestine's main function is to remove water from the undigested matter and form solid waste.

There are a variety of digestive problems that can be encountered along various portions of the gastrointestinal tract. In general, the motility of the gastrointestinal tract is based on intricate neurohormonal interactions resulting in the coordinated movement of the gut. Aberration of such motor function can result in common gastrointestinal motility disorders, such as gastroesophageal reflux disease (GERD) and gastroparesis.

Gastroesophageal reflux is a condition in which the weakness of the esophageal sphincter allows the acidic contents of the stomach to move backward up into the esophagus (FIG. 4). In some cases, gastroesophageal reflux is considered physiologic (reflux in normal individuals). This physiologic reflux occurs several times a day in otherwise healthy individuals without associated symptoms or damage. Gastroesophageal reflux is considered a disease (GERD) when the reflux produces frequent or severe symptoms that can cause damage to the esophagus, pharynx or respiratory tract. Complications of GERD include esophageal erosion, esophageal ulcer, esophageal stricture, and Barrett's esophagus. GERD can be attributed to such factors as transient lower esophageal sphincter (LES) relaxations, decreased lower esophageal sphincter (LES) resting tone, delayed stomach emptying, ineffective esophageal clearance, diminished salivation, potency of refluxed material, and the inability of the esophageal tissue to resist injury and repair itself. A weakened LES and transient spontaneous LES relaxation (relaxation not induced by swallowing) is a common cause of reflux (FIG. 5). Gastroesophageal reflux disease commonly results when the resting LES pressure is too low to resist the pressure within the stomach or when the normal angulation of the esophagogastric junction is lost (e.g. hiatus hernia) (FIGS. 6A-6B'). GERD is generally treated by lifestyle changes in combination with drug therapy. In some cases surgical intervention is used. Surgical intervention is aimed at strengthening and tightening the LES the antireflux barrier.

Achalasia is a rare disease of the esophagus muscles resulting in an inability of the LES to relax and open to let food pass into the stomach (FIGS. 7A-C). The esophagus contains both muscle and nerves. The nerves coordinate the relaxation and opening of the sphincters as well as the peristaltic waves in the esophagus. In aclasia, nerve cells located between the esophageal muscle layers are damaged. Individuals with achalasia have difficulty swallowing food. Botulinum toxin can be effective in improving symptoms of achalasia. Dilation using various dilator systems, such as balloon dilators, are also used to weaken the LES and allow food to pass.

Gastroparesis is a disorder in which the stomach takes too long to empty its contents. Gastroparesis happens when nerves of the stomach which control the movement of food through the digestive tract are damaged or stop working. The vagus nerve controls the movement of food through the digestive tract. If the vagus nerve is damaged, the muscles of the stomach and intestines do not work normally, and the movement of food is slowed or stopped. Gastroparesis most often occurs in people with type 1 diabetes or type 2 diabetes. However, up to one third of patients with gastroparesis have no identifiable cause of the disorder. Gastroparesis primarily is addressed by treating the underlying diseases causing gastroparesis. Medications to promote gastric emptying are also used. Endoscopically placed gastrostomy tubes can also be used to help drain the stomach.

Irritable bowel syndrome (IBS) is a common intestinal disorder that affects a person's colon and cause recurrent abdominal cramps, bloating, constipation, and diarrhea. The causes of IBS are not clear, but it is believed that a combination of factors can lead to symptoms of IBS, including visceral hypersensitivity, altered bowel motility, neurotransmitters imbalance, infection and psychosocial factors. There is no cure for IBS, but the symptoms may be treated by changing eating habits, reducing stress, and making lifestyle changes. Medications can also be taken to relieve diarrhea or constipation.

Other common GI tract disorders include those of the stomach and intestine, such as diarrhea and constipation. With diarrhea, muscle contractions move the contents of the intestines along too quickly and there isn't enough time for water to be absorbed. Constipation is the opposite, with the contents of the large intestines not moving along fast enough. Gastritis is an irritation and inflammation of the stomach lining by acids produced in the stomach.

While many gastrointestinal disorders can be treated with lifestyle changes and/or medications, some conditions may require surgery. One method for accessing the gastrointestinal tract include using open surgical techniques, which requires making a long incision down the center of the abdomen. Laparoscopic procedures are minimally invasive procedures wherein small "keyhole" incisions are made in the abdomen. Generally, three of more small (5-10 mm) incisions are made in the abdomen to provide access ports to various surgical instruments and a laparoscope, which transmits pictures on a video monitor. A person undergoing a laparoscopic procedure may experience less pain and scarring after surgery, and a more rapid recovery than with an open surgical procedure.

The gastrointestinal tract can also be accessed through the mouth (upper GI endoscopy) or anus (lower GI endoscopy: colonoscopy, sigmoidoscopy, enteroscopy) by inserting a flexible endoscope through the mouth or anus body cavity to the site of interest. Upper endoscopy involves the examination of the lining of the esophagus, stomach, and duodenum (first part of the small intestine) by insertion of a flexible endoscope through the mouth to the site. Lower endoscopy involves examination of the lining of the large intestine (colon). A conventional endoscope is shown in FIG. 9. The light source illuminates the pathway and site, while the camera transmits images to a monitor. Various instruments can be introduced through the instrument port.

SUMMARY OF THE INVENTION

The invention generally relates to devices and methods for implantation of one or more microstimulators at to any site within the gastrointestinal tract. The device can be employed using open, laparoscopic, and endoscopic techniques.

In one aspect, the invention generally relates to a device for implanting one or more microstimulators within one or more implantation sites in the gastrointestinal tract using endoscopic techniques. The device comprises an elongate body member having a proximal end and a distal end, the elongate body member being flexible along at least a portion of its length for insertion through the gastrointestinal tract. The distal end of the elongate body member is adapted for releasably holding one or more microstimulators. A handle is located at the proximal end of the elongate body member. An actuation mechanism is in connection with the one or more microstimulators for deploying the one or more microstimulators into the one or more implantation sites.

Embodiments according to this aspect of the invention can include the following features. The device can include a grasping mechanism for releasably grasping a microstimulator at the distal end of the elongate body member. The grasping mechanism can comprise two or more arms that are movable between an open position for loading and releasing a microstimulator and a closed position for grasping a microstimulator. The device can include a push rod movable longitudinally within the elongate body member in a proximal and distal direction, such that movement in a distal direction causes the push rod to engage and push the microstimulator out of the distal end into an implantation site. The device can include one or more channels in the elongate body member in connection with one or more apertures at the distal end such that injection of a fluid through the one or more channels causes the fluid to impinge upon and push the microstimulator out of the distal end into an implantation site. The device can include a ligation clip at the distal end of the elongate body member, the ligation clip releasably holding one or more microstimulator. In this embodiment, a grasping mechanism at the distal end of the elongate body member can be adapted for grasping the ligation clip. The grasping mechanism can comprise two or more arms that are movable between an open position and a closed position, wherein the open position is for loading a ligation clip and for loading and releasing a microstimulator from the ligation clip, and the closed position is for grasping the ligation clip and microstimulator. The ligation clip can have one or more apertures, and the device can further comprises one or more microstimulator push rods movable longitudinally within the elongate body member in a proximal and distal direction, such that movement in a distal direction causes the one or more microstimulator push rods to pass through one or more aperture in the ligation clip, and to engage and push the microstimulator out of the implantation device into an implantation site. The device can further comprise one or more ligation clip push rods movable longitudinally within the elongate body member in a proximal and distal direction, such that movement in a distal direction causes the one or more ligation slip push rods to engage and push the ligation clip out of the implantation device to the implantation site. The ligation clip can have one or more apertures, and the device can further comprise one or more microstimulator deploying channels in the elongate body member in connection with one or more apertures at the distal end and one or more apertures in the ligation clip such that injection of a fluid through the one or more microstimulator deploying channels causes the fluid to impinge upon and push the microstimulator out of the distal end into an implantation site. In this embodiment, the device can further comprise one or more ligation clip deploying channels in the elongate body member in connection with one or more apertures at the distal end such that injection of a fluid through the one or more ligation clip deploying channels causes the fluid to impinge upon and push the ligation clip out of the distal end into an implantation site.

In another aspect, the invention generally relates to a method for implantation of one or more microstimulators into one or more implantation sites in the gastrointestinal tract comprising using the device of any one of embodiments described herein for implantation of one or more microstimulators within the gastrointestinal tract.

Embodiments according to this aspect of the invention can include the following features. The method can include implantation of one or more ligation clips at the site of microstimulator implantation subsequent to implantation of one or more microstimulators.

In another aspect, the invention generally relates to a method for implantation of one or more microstimulators into one or more implantation sites in the gastrointestinal tract comprising endoscopically accessing an implantation site within the gastrointestinal tract using an endoscope; inserting a sclerotherapy needle through the endoscopic instrument channel to the implantation site; injecting saline or another suitable fluid into the submucosa to create a cushion of fluid into which the microstimulator will be implanted; inserting a cutting instrument through the endoscopic instrument channel to the implantation site; making an incision in the cushion through the mucosa and submucosa. for a length suitable to provide an opening through which the microstimulator can be implanted; inserting an implantation device in accordance with any one embodiments described herein through the endoscopic instrument channel to the implantation site; and deploying the microstimulator into incision in the implantation site.

Embodiments according to this aspect of the invention can include the following features. The method can include, after deploying the microstimulator into incision in the implantation site, pushing the implantation device against the microstimulator to further push the microstimulator into the implantation site. Once the microstimulator is in the implantation site, one or more ligation clips can be deployed to close the incision housing the microstimulator. One or more microstimulators are implanted within the gastrointestinal tract to treat GERD and/or the symptoms of GERD by implantation of one or more microstimulators in the lower esophageal sphincter. In treating GERD, one or more microstimulators can be implanted approximately 1-cm proximal to the gastroesophageal junction.

In another aspect, the invention generally relates to a method for treating GERD, gastroparesis, dumping syndrome, obesity, intestinal dysmotility, constipation, diarrhea, irritable bowel syndrome, pharyngeal dysfunction, fecal incontinence, and/or anal sphincter dysfunction comprising using the device of any one of the embodiments described herein to implant one or more microstimulators within the gastrointestinal tract.

Embodiments according to this aspect of the invention can include the following features. The method can include treatment of gastroparesis by implanting one or more microstimulators in the stomach. The method can include treatment of pharyngeal dysfunction by implantation of one or more microstimulators in the pharyngeal muscles. The method can include treatment of irritable bowel syndrome by implantation of one or more microstimulators in the colon. The method can include treatment of fecal incontinence by implantation of one or more microstimulators in the anal sphincter. The method can include treatment of obesity by implantation of one or more microstimulators in the stomach and/or small bowel. The method can include treatment of small bowel dysmotility by implantation of one or more microstimulators in the small bowel.

In another aspect, the invention generally relates to medical device kit comprising one or more of the devices of any of the embodiments described herein. One or more of the devices can be packaged in sterile condition.

Other aspects and advantages of the invention will become apparent from the following description, taken in conjunction with the accompanying drawings, illustrating the principles of the invention by way of example only.

BRIEF DESCRIPTION OF THE DRAWINGS

The foregoing and other objects, features, and advantages of the present invention, as well as the invention itself, will be more fully understood from the following description of various embodiments, when read together with the accompanying drawings.

FIG. 6A shows a normal esophagogastric (EG) junction.

FIG. 6A' shows an endoscopic view of a normal esophagogastric (EG) junction.

FIG. 6B shows a hiatus hernia

FIG. 6B' shows an endoscopic view of a hiatus hernia.

FIG. 7A shows anatomic findings in achalasia, with 7B showing an endoscopic image, and 7C showing a radiographic image.

FIGS. 11A and B show embodiments wherein the implantation device includes a push mechanism.

FIGS. 12 A-C show embodiments wherein the implantation device includes one or more fluid deployment channels.

FIGS. 13A-B show another embodiment of an implantation device including a grasping mechanism at its distal end.

FIGS. 14A-B shoe another embodiment of an implantation device including another type of grasping mechanism at its distal end.

FIGS. 17A-D shows an embodiment of an implantation device having a grasping mechanism for use with a ligation clip.

FIGS. 18A-C shows an embodiment of an implantation device for use with a ligation clip and having a push rod for deployment of the ligation clip.

As shown in FIGS. 19C-D, the ligation clip deploying body member can be slidably housed in the outer body member.

DESCRIPTION

Figure 1:
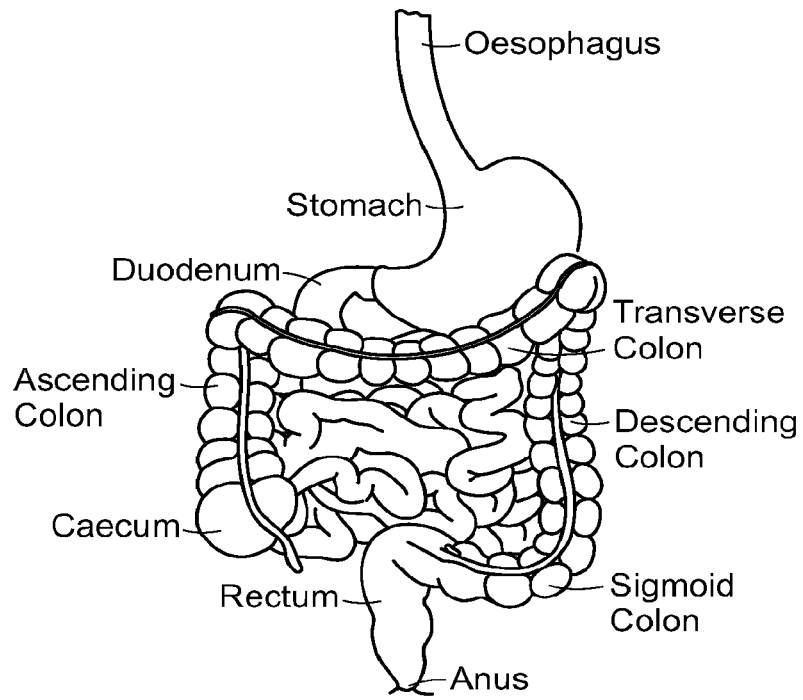
FIG. 1 shows the gastrointestinal tract.
Figure 2:
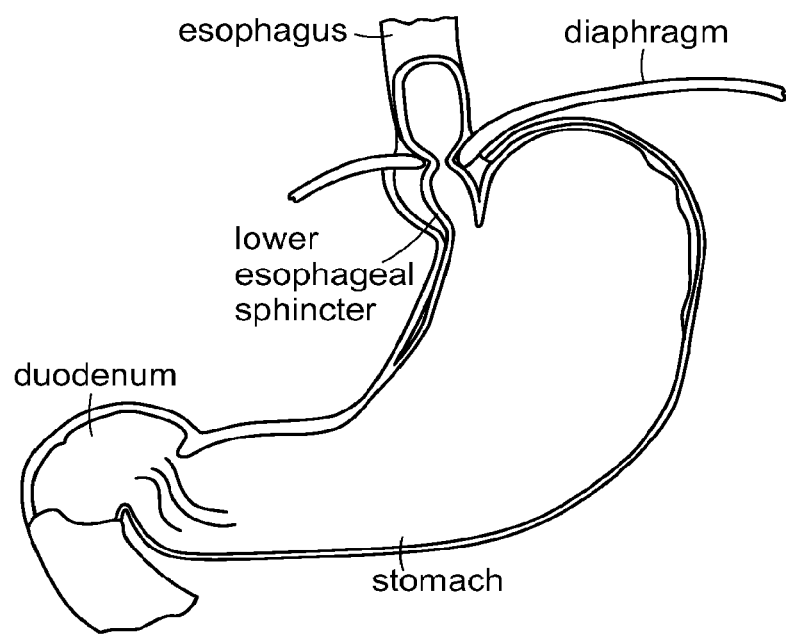
FIG. 2 shows a cutaway view of the GI tract from the esophagus to the duodenum.
Figure 3:
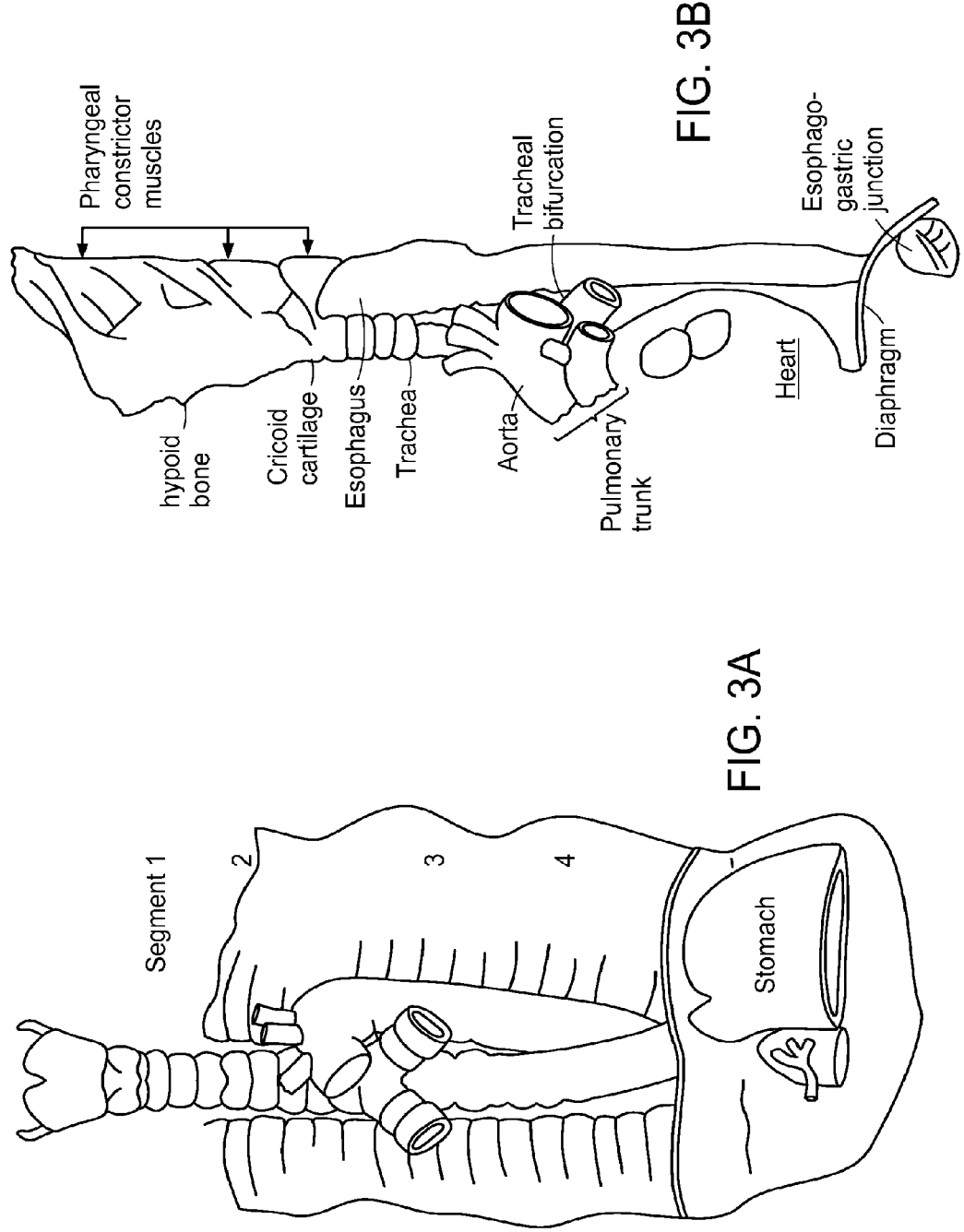
FIG. 3A shows the normal anatomy of the esophagus, anterior view.
FIG. 3B shows the normal anatomy of the esophagus, lateral view, showing the esophageal regions
Figure 4:
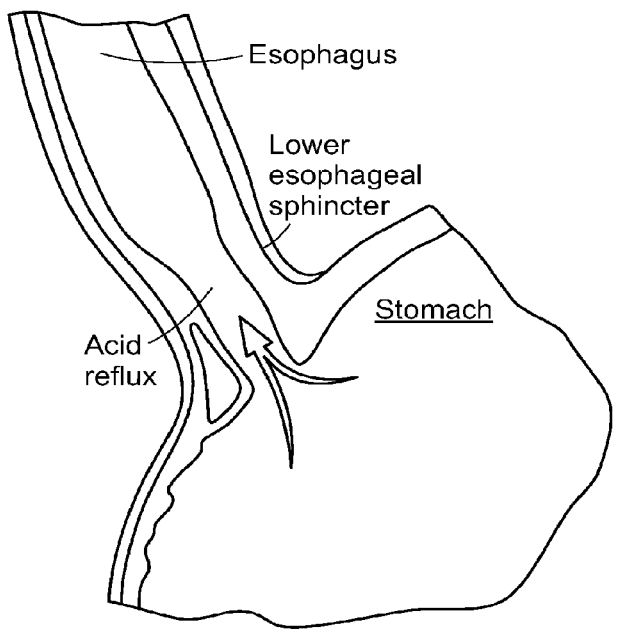
FIG. 4 shows the esophageal sphincter as it allows the acidic contents of the stomach to move backward up into the esophagus, as with gastroesophageal reflux.
Figures 5A, 5B:
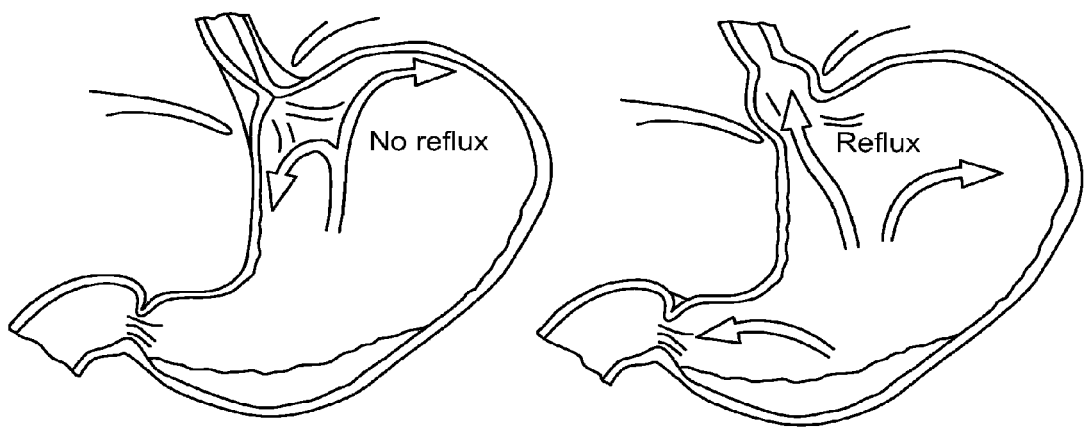
FIG. 5 shows the mechanism of gastroesophageal reflux.

Embodiments of devices and methods according to the invention can be used to access, diagnose, and treat various diseases within the entire GI tract including, but not limited to the mouth (oral cavity, which includes the salivary glands, mucosa, teeth, and tongue), the pharynx, the esophagus and cardia, the stomach (antrum and pylorus and pyloric sphincter), the small intestine (duodenum, the jejunum, and the ileum), the large intestine (the cecum, the colon—ascending colon, transverse colon, descending colon, and sigmoid flexure—and the rectum), and anus. Various diseases and disorders that the present devices and methods can access, diagnose, and treat include, but are not limited to, gastroesophageal reflux, achalasia, irritable bowel syndrome (IBS), diarrhea, constipation, gastroparesis, nausea, vomiting, gastrointestinal infections, small bowel dysmotility, gastritis, fecal incontinence, obesity, incontinence, and pharyngeal dysfunction. The devices and methods can be used in open, laparoscopic, and endoscopic procedures.

An underlying problem of gastrointestinal motility disorders is a neuromuscular imbalance resulting in a lack of stimulation to the muscles (e.g. sphincters, pacemaker cells, etc). When functioning properly, the muscles are stimulated by electrical signals that are communicated from the brain and spinal cord by way of muscle nerves. However, these electrical signals to the muscles can be abnormal or absent, resulting in various abnormalities, disorders, and diseases in the GI tract. The methods and devices of the present invention address the underlying neuromuscular problem by the use of microstimulators, which are implanted at one or more muscle sites. In some embodiments, the microstimulators are activated to stimulate or inhibit the activity of the desired muscles directly. In other embodiments, one or more microstimulators can be implanted in a muscle site near the nerves which control certain muscles and the muscles are stimulated or inhibited indirectly by activation of the nerves which control the muscles. A combination of direct and indirect stimulation/inhibition can also be used.

Another problem present in gastrointestinal disorders is a loss of tone of the muscles. In some embodiments, the microstimulators are implanted at one or more muscle sites and/or muscle sites hear the nerves which control the muscles. The microstimulators are used to increase or decrease the tone of gastrointestinal smooth muscle, thereby treating various motility disorders of the GI tract. For example, repeated activation of the muscles by microstimulators within the muscles and/or via the nerves which control the muscles enables the muscles to retain and/or develop bulk and tone.

In some embodiments, the methods and devices of the present invention are used to implant one or more microstimulators using open surgical procedures. In other embodiments, the methods and devices of the present invention are used to implant one or more microstimulators using laparoscopic procedure. Laparoscopic procedures are less invasive than surgery, but require skin and abdominal wall incision, and can cause operating wound hernias and other complications. Minimally invasive endoscopic procedures through the GI tract are generally preferable because such methods do not require that skin and abdominal wall incisions be made to access the GI tract, are less invasive than laparoscopy, and can be done as out-patient procedure.

Microstimulators are well-known, and the general features of the implantable microstimulators of the present invention can be in accordance with these conventional microstimulators. In some embodiments, the microstimulators are inserted within the body and are activated remotely outside of the body to produce a localized electrical current pulse having variable magnitude, duration, and rate of repetition. Presently available microstimulators, such as the BION® microstimulator, can used. The BION® microstimulator is an injectable RF powered single-channel stimulator that is encased with ceramic. The BION® microstimulators receive power and are activated via a magnetic link from an external coil that is worn by the patient. The BION® microstimulator and other currently available microstimulators are generally elongate in shape with electrodes at each end that deliver the electrical current. The body of the microstimulators is made up of a rigid dielectric material, such as glass or ceramic, capable of transmitting magnetic fields. The microstimulators are further hermetically sealed to protect the device from body fluids and water vapor. The BION® microstimulator is approximately 16 mm in length and 2.4 mm in outer diameter. Other known microstimulators that are remotely activated have similar dimensions, and these microstimulators are rigid along their lengths.

The microstimulators are inserted into the GI tract and implanted in the desired muscle and/or nerve site using an implantation device 100. Various embodiments of the implantation device are shown in FIGS. 10A-19D. In some embodiments, the implantation device 100 is similar in design to conventional surgical clip appliers, ligating clip appliers, or hemostatic clip appliers and, thus, the general features of the implantation device can be in accordance with these appliers. These various appliers are used to hold and guide one or more clips to a site within the body and are actuated to discharge one or more clips from the applier into a desired site in the body. The clips are used to ligate tissues and body vessels during various procedures. Thus, in some embodiments, as described herein in more detail, these various appliers can suitably be modified so as to hold and guide one or more microstimulators to a site within the body and actuated to discharge one or more microstimulators into a desired body site. In other embodiments, as described herein in more detail, these various appliers can be used to hold one or more ligation clips which, in turn, each hold one or more microstimulators. The appliers can then be used to discharge the microstimulators and, subsequently, discharge one or more ligation clips.

As shown in the figures, the implantation device has an elongate body member 1 having a proximal end 2 and a distal end 3. A handle 5 can be located at the proximal end 2 of the elongate body member 1.

The handle 5 can be in any form and suitably can be provided with a rubber coating, grooves or similar finger grip configuration (e.g., surface preparations or artifacts) to assist or facilitate the surgeon in securely gripping the instrument.

The elongate body member 1, as shown in the figures, has a generally cylindrical shape with a circular cross-section. However, this shall not be construed as limiting the body to such as shape, as it is within the scope of the present invention for other geometric shapes to be used for the body member 1 such as, for example, an oval, square, hexagon or other cross-sectional shapes. The body member 1 can be provided with a smooth outer surface so as to prevent or minimize damage that could result if the body member 1 contacts tissues or other internal and external structures and so as to allow for a smooth manipulation of the body member 1 within an endoscope's instrument port. At least a portion of the length of the elongate body member is flexible for insertion through an endoscope which has been inserted within the GI tract.

The length of the elongate body member 1 can be in accordance with the lengths of known instruments that are inserted through an endoscope to any point in the GI tract. The lower range of lengths generally range from about 20 cm to about 100 cm, while the upper range of lengths generally range from about 100 cm to about 200 cm. In some embodiments, the implantation device 100 is designed to access any portion of the GI tract through using either upper or lower endoscopic techniques and, as such, is sized sufficiently long so as to reach all portions of the GI tract using such techniques. In other embodiments, a plurality of implantation devices are custom designed to access certain areas of the GI tract by providing an elongate body member having a length that is based on the site within the GI tract the device is used to access. For example, a plurality of implantation devices can be provided, each having an elongate body adapted for accessing different parts of the GI tract (e.g. one implantation device can be provided with a length specifically adapted for accessing the LES using upper endoscopy, while another device can be adapted for accessing the upper portion of the colon using lower endoscopy). Thus, a plurality of implantation devices 100 can be provided, each having different length body members 1 adapted for accessing different parts of the GI tract. In other embodiments, an implantation device 100 can be provided with a handle 5 having a plurality of removable and interchangeable elongate body members 1 of different lengths. Conventional connection mechanisms that can provide repeat connection and removal between the removable interchangeable elements (e.g. handle 5 and body member 1) can be used in these embodiments (e.g. mating threaded portions and mating tabs and grooves). Still further, various types of interchangeable handles 5 (e.g. actuating and non-actuating handles) can be provided The outer diameter of the elongate body member can also be in accordance with typical outer diameters of instruments inserted through an endoscope within the GI tract. Conventional endoscopes generally have working channels with a diameter up to 4.2 mm. The elongate body member 1, thus, is sized so as to fit within the working channel of any endoscope and to allow for manipulation of the elongate body member within the working channel.

The elongate body member 1 is further adequately flexible so that it can traverse the complex pathway of the GI tract, but at the same time, it cannot be so flexible that it will buckle if it encounters a curve. As such, the elongate body member 1 can be fabricated from any material as is known to those skilled in the art for use in fabricating such surgical instruments that are inserted through endoscopes within the GI tract. Such materials are generally biocompatable materials having sufficient flexibility to traverse the pathway of the GI tract. In some embodiments, the flexibility is provided, at least in part, by forming the body member 1 of a sufficiently thin diameter and/or with sufficiently thin walls. In other embodiments, the body member 1 can be formed of a flexible polymeric material. In some embodiments, the body member 1 further includes one or more backbones (for example, a wire or the like) that can be implanted within the body member 1 or that can run along the outer surface of the elongate body member, so as to provide structural support to the body member 1.

The distal end 3 of the elongate body member 1 is designed so as to releasably grasp or house a microstimulator. The microstimulator can be directly grasped or housed by the distal end 3 or, in some embodiments, it can be indirectly grasped or housed via a ligation clip as described herein in more detail.

Figure 10A:
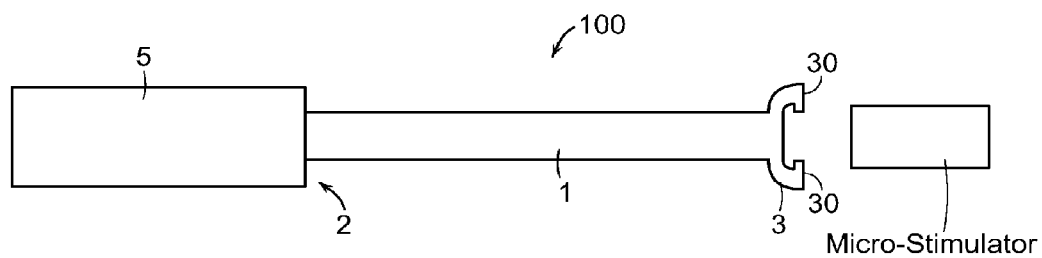
FIG. 10A shows an embodiment of an implantation device used to implant one or more microstimulators in accordance with the invention.
Figure 10B:
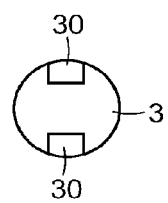
FIGS. 10B, C, and F-H show an embodiments of the distal end having tabs for grasping a microstimulator.
Figure 10C:
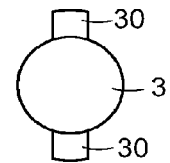
FIGS. 10D and 10E show an embodiment of a collar having depressions for mating with tabs, the collar being mountable on a microstimulator.
Figure 10D:
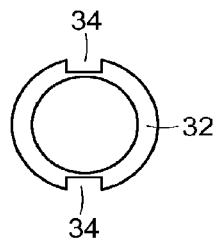
Figure 10E:
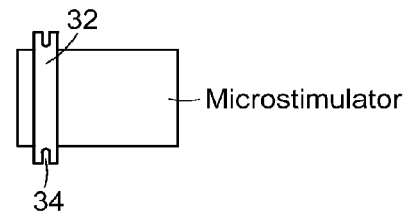
Figure 15:
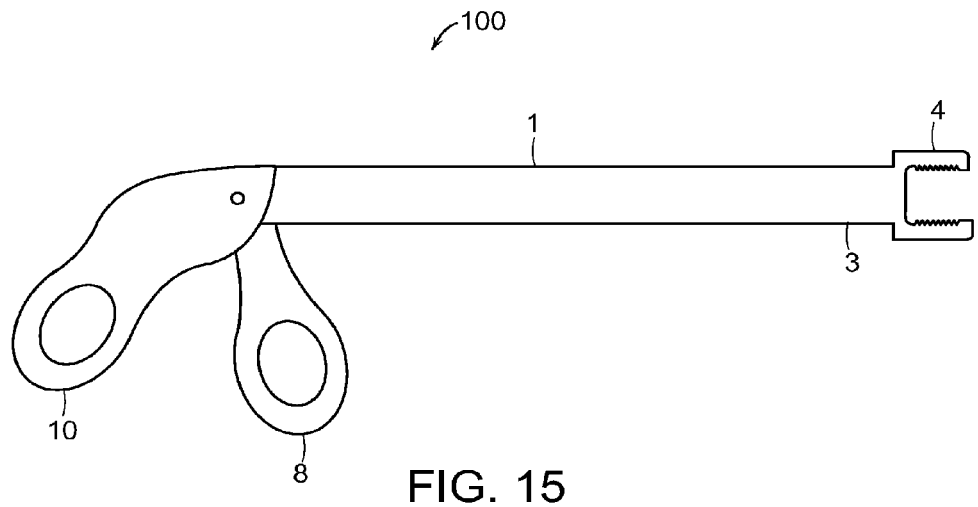
FIG. 15 shows another embodiment of an implantation device used to implant one or more microstimulators in accordance with the invention, wherein the handle is in the form of an actuation handle having finger and thumb rings.

In one embodiment, for example, as shown in FIGS. 10A-F, the distal end 3 is designed so as to releasably grasp the microstimulator, for example, using tabs or the like. For example, one or more tabs 30 can extend from the distal end for grasping the microstimulator about its circumference, for example, as shown in FIG. 10E. In some embodiments, the microstimulator can further be designed with mating depressions with which the tabs interconnect, and the tabs can be adjusted to a closed position within these depressions. In other embodiments, a microstimulator collar 32 having mating depressions 34 can be provided for placement on the microstimulator (FIGS. 10D-E). The tabs 30 can be movable between an open (FIG. 10C) and closed (FIG. 10B) position for holding and releasing the microstimulator. In some embodiments, a button 6 or similar activation mechanism in connection with tabs can be positioned on the handle 5 for actuating the tabs between an open and closed position. The tabs 30 can be sensitive to pressure such that application of pressure on the tabs 30 depresses them within the distal end (e.g. FIG. 10G) and absence of pressure causes them to extend outside of the distal end for engagement with the microstimulator and/or collar (e.g. FIG. 10H).

In some embodiments, the implantation device includes a microstimulator deployment mechanism for deploying a microstimulator from the elongate body member 1 into the implantation site. Any conventional deployment mechanism, such as those used to deploy clips from various clip applicators could be used. For example, in one embodiment, as shown in FIGS. 11A-B, a push rod or similar pushing mechanism 40 is movably housed within the elongate body member 1. The pushing mechanism 40 is movable longitudinally in a proximal and distal direction such that actuation of the pushing mechanism 40 in a distal direction causes the pushing mechanism 40 to engage and deploy the microstimulator from the implantation device. In these embodiments, the microstimulator can be held by the distal end, for example, by friction, such that engagement by pushing mechanism moves the microstimulator away from implantation device to the implantation site. A button 6 or other type of activation mechanism for activating the pushing mechanism 40 can be in connection with the pushing mechanism for moving the pushing mechanism 40 longitudinally in a proximal or distal direction. A spring or the like can be suitably be used to interconnect the pushing mechanism and button.

In other embodiments, the elongate body member 1 can include one or more channels 46 extending through the distal end. A syringe or other fluid injection device can be connected to the device via a fluid injection port 44 positioned on the handle 5 or along the elongate body member 1. Water or other suitable fluids are injected through the one or more channels 46 and flows out of one or more apertures 48 in the distal end 3, thereby applying force to the microstimulator, which ejects the microstimulator from the implantation device into the implantation site (FIG. 12B).

In yet other embodiments, a grasping mechanism 4 is further located at the distal end 3 of the elongate body member 1, as shown, for example, in FIGS. 13A-17D. The grasping mechanism 4 is adjustable between a closed, grasping configuration (e.g. FIGS. 13A and 14A) and an open configuration (e.g. FIGS. 13B and 14B). To load the implantation device with a microstimulator, the grasping mechanism 4 is adjusted to an open configuration. The grasping mechanism 4 is then positioned about the microstimulator. The grasping mechanism 4 is then adjusted to a closed position so as to take hold of and grasp the microstimulator. The microstimulator can then be guided to its desired implantation site using the implantation device. Once at the implantation side, the grasping mechanism 4 is adjusted to an open configuration and the implantation device is pulled away from or withdrawn from the implantation site leaving the microstimulator in place. If necessary, the front of the grasping mechanism 4 can then be pushed against the microstimulator to further push it into the implantation site if necessary. Any conventional grasping mechanism 4 can be used such as one or more pairs of arms or jaws that are movable with respect to each other. In some embodiments, the grasping mechanism includes ridges or grooves, or similar gripping configurations to assist in securely grasping the microstimulator (see FIGS. 13A-14B)

In these embodiments, wherein a grasping mechanism 4 is used, the handle 5 can take on a variety of forms which provide actuation of the arms or jaws of the grasping mechanism 4. FIGS. 13A-14B shows one embodiment of a handle 5 being generally cylindrical or rectangular in overall shape. An actuating mechanism can be located at any point along the handle 5 for manipulating the grasping mechanism 4. For example, a button or trigger 6 can be located at the end of the handle 5 as shown in FIG. 13A-14B. The button or trigger 6 can, for example, be depressed to open or close the grasping mechanism 4 as desired, or can be rotated in one direction or the other to open or close the grasping mechanism 4 as desired.

In another embodiment, the handle 5 can be in the form of an actuating handle such as those used with various laparoscopic instruments having manipulatable distal ends. For example, laparoscopic dissectors, scissors, and similar instruments having an adjustable distal end include a grasping mechanism 4 in the form of jaws or the like, which are adjustable towards and away from each other for grasping and releasing various objects often have an actuating handle similar to the handle of scissors which includes finger and thumb rings 8, 10 (see FIG. 15). Finger and thumb rings 8, 10 can move alone or in combination with respect to each other to enable, for example, grasping of a targeted object.

Figure 16:
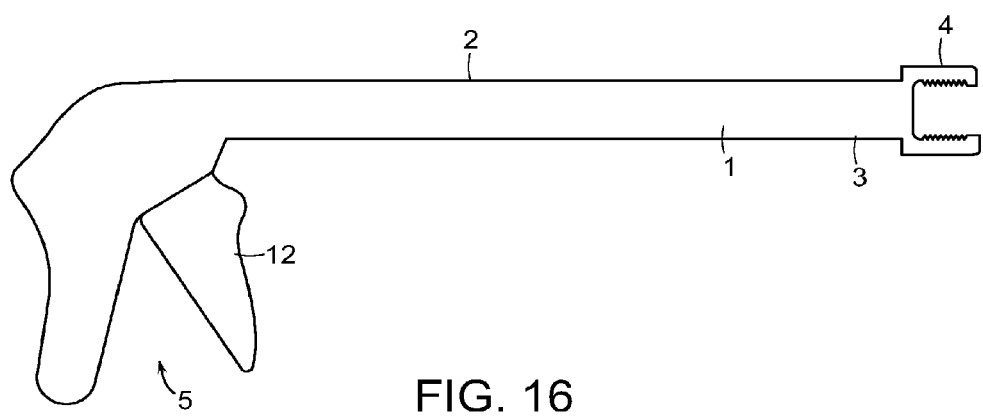
FIG. 16 shows another embodiment of an implantation device used to implant one or more microstimulators in accordance with the invention, wherein the handle is in the form of an actuation handle having a trigger.

In other embodiments, the actuating handle can include a trigger 12 that can be depressed or released to manipulate the grasping mechanism 4 (see FIG. 16).

In some embodiments, the implantation device 100 is designed so as to hold a ligation clip 50 which, in turn, holds the microstimulator. In these embodiments, the implantation device can be in the general form of conventional clip applicators, and being modified as desired so as to accommodate the microstimulator within the ligation clip. Commercially available ligation clips include those known as the EndoClip II and Ligaclip ERCA. The ligation clips are formed of biocompatable materials having sufficient flexibility to allow for opening and closing of the arms of the ligation clip. Materials used in forming ligation clips include for example, titanium and steel. The ligation clips in accordance with the present invention are suitably sized so as to grasp and hold a microstimulator for insertion through the GI tract and so as to release the microstimulator within and/or at an implantation site.

For example, in one embodiment, as shown in FIGS. 17A-B, a design similar to the above-described implantation devices 100 having grasping mechanisms 4 is used. In these embodiments, the grasping mechanism 4 can be designed to hold the ligation clip. The ligation clip holds the microstimulator. As the grasping mechanism 4 is actuated to open the arms or jaws, the ligation clip, likewise, opens to release the microstimulator. Withdrawal of the implantation device 100 away from the implantation site leaves the microstimulator in place at the implantation site. The microstimulator can further be pushed into the implantation site using the grasping mechanism 4 or ligation clip 50.

In another embodiment, the implantation device 100 is similar to those shown and described in FIGS. 11A-12B except that the distal end 3 of the elongate body member 1 grasps or houses the ligation clip 50. The ligation clip can have one or more apertures through which a pushing mechanism 40 passes to engage microstimulator or through which fluid can pass to impinge on microstimulator, for example, as shown in FIGS. 18A-B.

In certain embodiments, wherein a ligation clip 50 is used to grasp the microstimulator, the ligation clip 50 can be further deployable into the tissues surrounding the implanted microstimulator so as to seal the microstimulator within the implanted tissues. Thus, for example, upon insertion of the microstimulator into the implantation site, the ligation clip can be deployed into the tissues in accordance with conventional mechanisms and methods. In one embodiment, for example, a second pushing mechanism 41 is provided for deploying ligation clip, for example, as shown in FIG. 18C. In another embodiment, one or more ligation clip deploying channels (not shown) are provided for injection of a fluid for impingement on and deployment of the ligation clip 50 similar to deployment of the microstimulator using fluid.

Figure 19A:
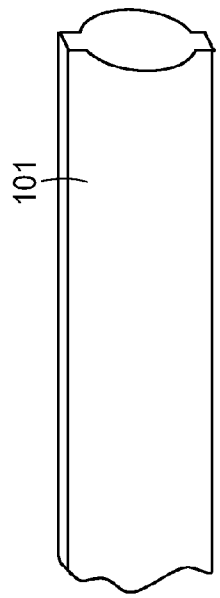
FIGS. 19A-D show an embodiment of a dual elongate body member, wherein the outer body member houses a ligation clip deploying body member.
Figure 19B:
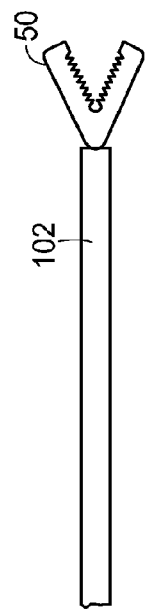
Figure 19C:
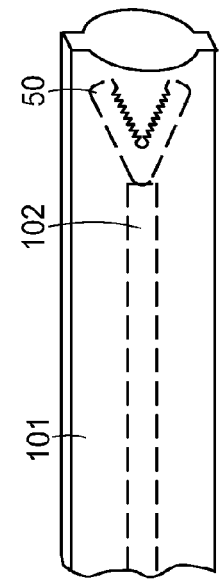
Figure 19D:
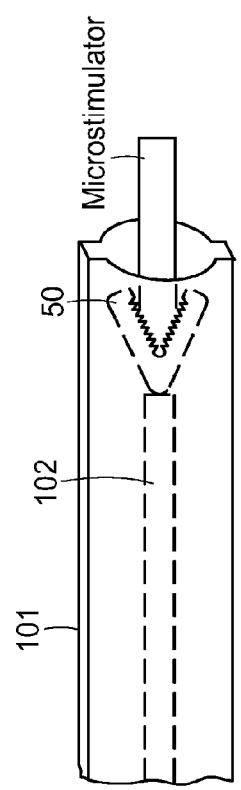

In another embodiment, the implantation device 100 includes a hollow outer elongate body member 101 (FIG. 19A) through which an inner elongate body member for grasping and holding the ligation clip (FIG. 19B) is slidably housed, for example, as shown in FIGS. 19C-D. Deployment of the microstimulator and ligation clip can be in accordance with any of the deployment mechanisms described herein.

Methods of the present invention comprise implanting one or more microstimulators into any area of the GI tract using any of the embodiments of the implantation device 100. The methods can be performed using open, laparoscopic, or endoscopic techniques.

Figure 8:
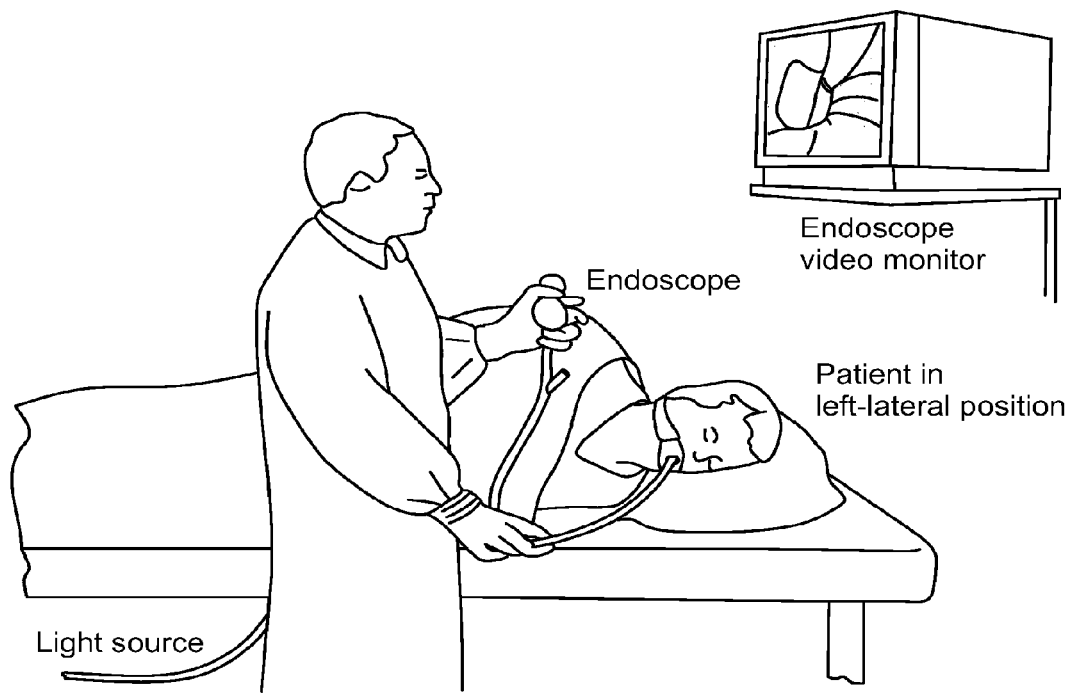
FIG. 8 shows common patient positioning for an endoscopy.
Figure 9:
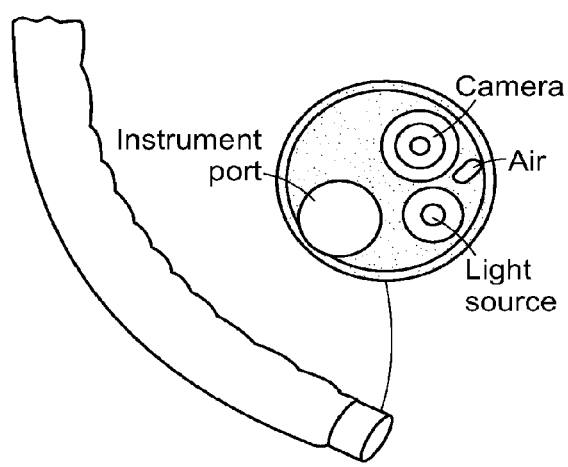
FIG. 9 shows a conventional endoscope.
Figure 20:
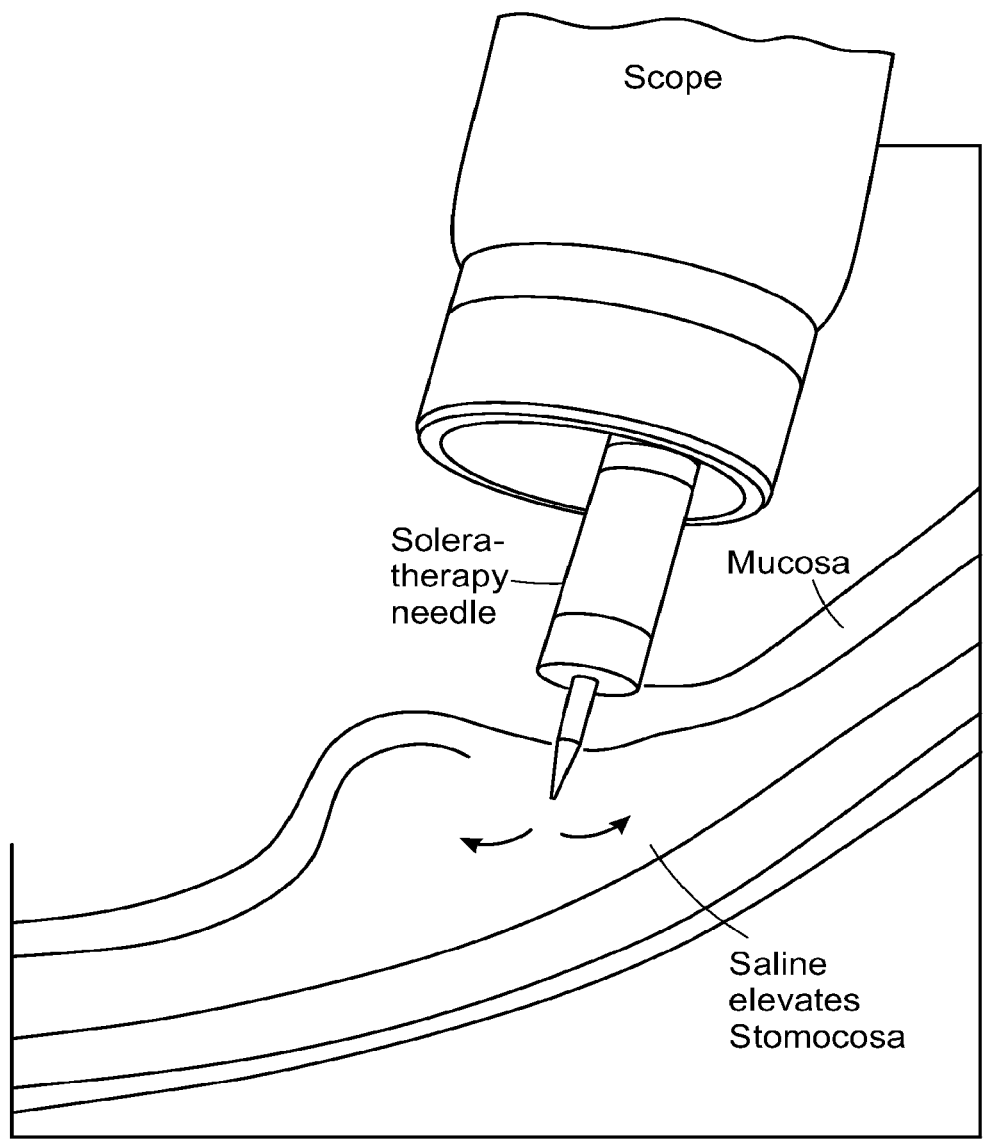
FIG. 20 shows injection of saline into the submucosa.

In one embodiment, one or more microstimulators are implanted using an upper endoscopic technique. Before insertion of the endoscope, a patient may be given a pharyngeal anesthetic to help prevent gagging. Pain medication and a sedative may also be administered. The patient is placed in the left lateral position and the endoscope is passed through the mouth and pharynx and into the esophagus (see FIG. 8). The implantation site is identified endoscopically. A sclerotherapy needle is inserted through the endoscopic instrument channel to the site(s) where microstimulator(s) will be implanted, and is used to inject saline or other suitable fluids into the submucosa (see e.g. FIG. 20). In some embodiments, approximately 5-15 cc saline are injected. The injection of fluid into the submucosa creates a cushion of fluid into which the micro-stimulator can be implanted. An incision is made in the cushion through the mucosa and submucosa. For example, a needle-knife can be inserted through the endoscopic instrument channel and used with a blended setting to make an initial incision (e.g. a 5 mm incision). The needle knife is then gently pushed along the tract between the submucosa and muscularis propria for a length suitable to provide an opening through which the microstimulator can be implanted (for example, approximately 20 mm in some embodiments). The microstimulator is loaded into the implantation device 100, and the micro-stimulator is then gently inserted into the GI tract with the implantation device 100. Once the microstimulator reaches the implantation site, any of the deployment mechanisms can be used to deploy the microstimulator from the implantation device 100 into or at the incision at the implantation site. The implantation device 100 is withdrawn away from the microstimulator and, if needed, the implantation device 100 (e.g. the distal end) can be pushed against the microstimulator to help lodge the microstimulator in place.

In embodiments wherein the implantation device 100 incorporates a ligation clip 50, the ligation clip 50 can subsequently positioned at the incision in which the microstimulator is implanted. One or more ligation clips 50 can then be used to close the incision housing the microstimulator.

Figure 21:
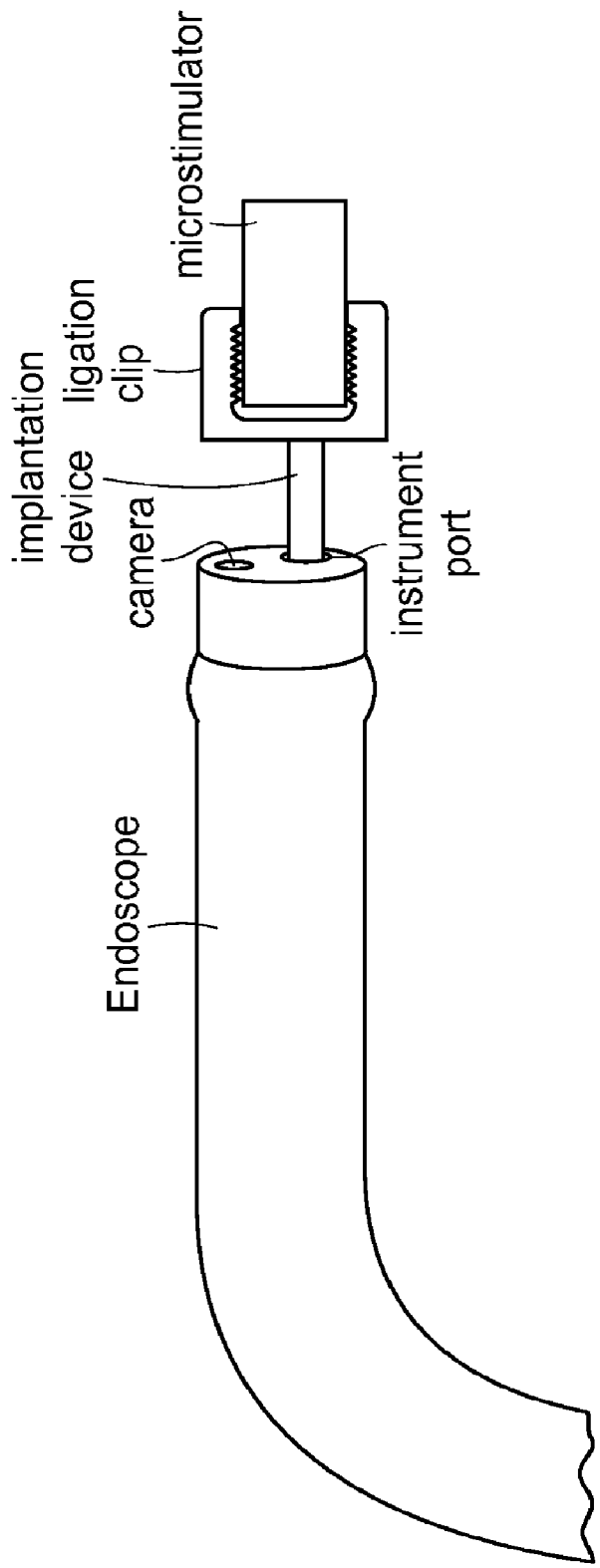
FIG. 21 shows front-loading of the microstimulator.

In embodiments, the microstimulator is of a design that does not allow for insertion to the GI tract implantation site through the endoscopic instrument channel. For example, the size and/or rigidity of the microstimulator may not allow for insertion through an endoscopic instrument channel when the endoscope is in position within the complex and tortuous pathway of the GI tract. In such embodiments, the following front-loading method can be used to guide the microstimulator to the GI tract implantation site and implant the microstimulator at the site. After the endoscope is inserted to the implantation site, the saline injected, and incision made, the endoscope is withdrawn from the body of the patient. The implantation device 100, without the microstimulator, is inserted through the endoscope instrument port until the distal end 3 extends outside the endoscope instrument port. The implantation device 100 is then loaded with the microstimulator and, if used, one or more ligation clips (a plurality of ligation clips can be housed within the body member 1, for example, as with conventional ligation clip applicators). The entire apparatus, including the endoscope, implantation device 100, microstimulator, and ligation clip(s), if used, is then inserted through the patient's mouth to the implantation site with the microstimulator protruding beyond the distal end of the endoscope (e.g. as shown in FIG. 21). Once at the site, the microstimulator is then implanted into the incision at the implantation site as described herein. Ligation clips can subsequently be implanted as desired.

In certain embodiments, the endoscope can include two instrument ports and channels through which instruments can be inserted and manipulated. As such, in some embodiments, a first channel can be used for injecting saline and making the incision, while a second channel can be used to implantation of microstimulators and ligation clips. Further, once the saline is injected and the incision made, the first channel can also be used for implantation of microstimulators and ligation clips. In embodiments wherein the front-loading technique is used, prior to inserting the endoscope into the GI tract to the site for injection of saline and forming the incision in which the microstimulator is implanted, the microstimulator can be front loaded as discussed, and the entire device can then be inserted into the GI tract and the procedure can be performed without removal and reinsertion of the endoscope after the saline is injected and the incision formed.

In accordance with one method, GERD and/or the symptoms of GERD are treated by implantation of one or more microstimulators in the lower esophageal sphincter. In one embodiment, in the case of LES implantation, the site of implantation can be approximately 1-cm proximal to the gastroesophageal junction. Any number of microstimulators can be implanted at random or evenly spaced locations. Before or as a person eats a meal, the microstimulator(s) are turned on. The microstimulator(s) stimulate the muscle directly or indirectly by nerve stimulation (which, in turn, stimulates the muscle) so as to increase lower esophageal sphincter pressure and reduce GERD. After the meal is digested into the small intestine, the microstimulator can be turned off.

The methods and devices of the present invention are useful in altering sphincteric pressures as desired so as to treat multiple gastrointestinal disorders including, but not limited to: GERD, gastroparesis, dumping syndrome, obesity, intestinal dysmotility, constipation, diarrhea, irritable bowel syndrome, and anal sphincter dysfunction. The location at which the microstimulators are implanted will depend on the particular disease or disorder than is being targeted. For example, with gastroparesis, one or more microstimulators are implanted in the stomach. For pharyngeal dysfunction, one or more microstimulators are implanted in the pharyngeal muscles. For irritable bowel syndrome, one or more microstimulators are implanted in the colon. For fecal incontinence, one or more microstimulators are implanted in the anal sphincter. For obesity, one or more microstimulators are implanted in the stomach and/or small bowel. For small bowel dysmotility, one or more microstimulators are implanted in the small bowel The ability to have a therapeutic response will depend on implanting the micro-stimulators at the appropriate and strategically placed site. To treat GERD, the LES is stimulated and, thus, the microstimulator will be placed at the lower esophageal sphincter.

In another embodiment, one or more microstimulators are implanted into the GI tract in the LES so as to increase the tone of the LES. By increasing the tone of the lower esophageal sphincter, gastroesophageal reflux can be decreased.

In another embodiment, one or more microstimulators are implanted into the GI tract so as to improve abnormally slow gastric emptying in patients with gastroparesis, nausea, vomiting.

In another embodiment, one or more microstimulators are implanted in the colon so as to normalize abnormally slow small bowel and large bowel peristalsis in patients with constipation and irritable bowel syndrome.

In another embodiment, one or more microstimulators are implanted in the colon so as to inhibit abnormally fast peristaltics with diarrhea and irritable bowel syndrome.

In another embodiment, one or more microstimulators are implanted in the esophagus so as to relax persistently contracted muscle such as to treat patients with achalasia.

The present invention also includes kits that comprise one or more implantation devices of the present invention, preferably packaged in sterile condition. Such kits may include written instructions for use of the device and other components of the kit (e.g. microstimulators, ligation clips, interchangeable elongate body members 1, microstimulator collars, etc.)

Although the instruments and methods of the present invention are primarily illustrated and described herein by means of instruments which have been adapted for performing endoscopic microstimulator implantation within the GI tract of humans, it will be appreciated by those skilled in the art that such instruments and methods also are adaptable for use in both open and laparoscopic procedures as well as in performing various veterinary surgeries as well as implantation of microstimulators in other areas of the body. Further, while a preferred embodiment of the invention has been described using specific terms, such description is for illustrative purposes only, and it is to be understood that changes and variations may be made without departing from the spirit or scope of the following claims.

What is claimed is:

1. A device for implanting one or more microstimulators within one or more implantation sites in the gastrointestinal tract using laparoscopic techniques comprising:
   a rigid elongate body member having a proximal end and a distal end;
   a ligation clip releasably held at the distal end of the elongate body member;
   one or more microstimulators releasably held by the ligation clip at the distal end of the elongate body member;
   a handle at the proximal end of the elongate body member; and
   an actuation mechanism in connection with the ligation clip and the one or more microstimulators and configured for deploying the one or more microstimulators into the one or more implantation sites and for subsequently deploying the ligation clip.

2. The device of claim 1 wherein the distal end of the elongate body member includes a grasping mechanism for releasably grasping the ligation clip.

3. The device of claim 2 wherein the grasping mechanism comprises two or more arms that are movable between an open position for loading and releasing the ligation clip and a closed position for grasping the ligation clip.

4. The device of claim 1 further comprising a push rod movable longitudinally within the elongate body member in a proximal and distal direction, such that movement in a distal direction causes the push rod to engage and push the one or more microstimulators and/or ligation clip out of the distal end to an implantation site.

5. The device of claim 1 further comprising one or more channels in the elongate body member in connection with one or more apertures at the distal end such that injection of a fluid through the one or more channels causes the fluid to impinge upon and push the one or more microstimulators and/or ligation clip out of the distal end to an implantation site.

6. The device of claim 1 wherein the grasping mechanism comprises two or more arms that are movable between an open position and a closed position, wherein the open position is for loading the ligation clip and for loading and releasing the one or more microstimulators from the ligation clip, and the closed position is for grasping the ligation clip and the one or more microstimulators.

7. The device of claim 1, wherein the ligation clip has one or more apertures, and the device further comprises one or more microstimulator push rods movable longitudinally within the elongate body member in a proximal and distal direction, such that movement in a distal direction causes the one or more microstimulator push rods to pass through one or more aperture in the ligation clip, and to engage and push the microstimulator out of the implantation device into an implantation site.

8. The device of claim 1 further comprising one or more ligation clip push rods movable longitudinally within the elongate body member in a proximal and distal direction, such that movement in a distal direction causes the one or more ligation clip push rods to engage and push the ligation clip out of the implantation device to the implantation site.

9. The device of claim 1, wherein the ligation clip has one or more apertures, and the device further comprises one or more microstimulator deploying channels in the elongate body member in connection with one or more apertures at the distal end and one or more apertures in the ligation clip such that injection of a fluid through the one or more microstimulator deploying channels causes the fluid to impinge upon and push the one or more microstimulators out of the distal end into an implantation site.

10. The device of claim 9 further comprising one or more ligation clip deploying channels in the elongate body member in connection with one or more apertures at the distal end such that injection of a fluid through the one or more ligation clip deploying channels causes the fluid to impinge upon and push the ligation clip out of the distal end into an implantation site.

11. A method for treating a disease within the gastrointestinal tract comprising:
   laparoscopically accessing an implantation site within the gastrointestinal tract;
   using the device of claim 1 to deploy one or more microstimulators at the implantation site in the gastrointestinal tract; and
   activating the one or more microstimulators to stimulate or inhibit activity of one or more muscles directly, or activating the one or more microstimulators to stimulate one or more nerves which then stimulate or inhibit activity of the one or more muscles,
   whereby the stimulating or inhibiting activity of the one or more muscles by the one or more microstimulators provides proper functioning of the one or more muscles, thereby treating the disease.

12. The method of claim 11, wherein the method further comprises after deploying one or more microstimulators at the implantation site, using the device of claim 1 to implant one or more ligation clips at the implantation site thereby sealing the one or more microstimulators within the implantation site.

13. The method of claim 11, further comprising, prior to deploying one or more microstimulators at the implantation site, injecting saline or another suitable fluid into the submucosa at the implantation site to create one or more cushions of fluid into which or more microstimulators will be implanted.

14. The method of claim 11, wherein the disease treated is GERD, achalasia, gastroparesis, dumping syndrome, obesity, intestinal dysmotility, constipation, diarrhea, nausea, vomiting, gastrointestinal infections, gastritis, incontinence, irritable bowel syndrome, pharyngeal dysfunction, fecal incontinence, or anal sphincter dysfunction, and the step of implanting the one or more microstimulators comprises implanting the one or more microstimulators at one or more muscle sites associated with the disease.

15. The method of claim 14, wherein the one or more microstimulators are implanted in the lower esophageal sphincter to treat GERD.

16. The method of claim 15, wherein the one or more microstimulators are implanted approximately 1 cm proximal to the gastroesophageal junction.

17. The method of claim 11, wherein the one or more microstimulators are activated to stimulate the esophageal sphincter so as to increase lower esophageal sphincter pressure.

18. The method of claim 11, wherein the one or more microstimulators are activated to stimulate the esophageal sphincter so as to alter sphincteric pressure, thereby treating the disease.

19. The method of claim 11, wherein the one or more microstimulators are implanted in the stomach to treat gastroparesis.

20. The method of claim 11, wherein the one or more microstimulators are implanted in the pharyngeal muscles to treat pharyngeal dysfunction.

21. The method of claim 11, wherein the one or more microstimulators are implanted in the colon to treat irritable bowel syndrome.

22. The method of claim 11, wherein the one or more microstimulators are implanted in the anal sphincter to treat fecal incontinence.

23. The method of claim 11, wherein the one or more microstimulators are implanted in the stomach and/or small bowel to treat obesity.

24. The method of claim 11, wherein the one or more microstimulators are implanted in the intestine to treat intestinal dysmotility.

25. The method of claim 11, wherein the step of activating the one or more microstimulators comprises repeatedly activating the one or more microstimulators to repeatedly activate the one or more muscles directly or to repeatedly activate the one or more nerves which then stimulate or inhibit activity of the one or more muscles, wherein the repeated activation retains and/or develops bulk and tone of the muscles.

* * * * *